United States Patent [19] [11] Patent Number: 5,932,714
Loosmore et al. [45] Date of Patent: Aug. 3, 1999

[54] EXPRESSION OF GENE PRODUCTS FROM GENETICALLY MANIPULATED STRAINS OF BORDETELLA

[75] Inventors: Sheena M. Loosmore, Aurora; Reza Khayyam Yacoob, Mississauga; Gavin Ross Zealey, Thornhill; Michel Henri Klein, Willowdale, all of Canada

[73] Assignee: Connaught Laboratories Limited, North York, Canada

[21] Appl. No.: 08/472,171

[22] Filed: Jun. 7, 1995

Related U.S. Application Data

[63] Continuation of application No. 08/393,334, Feb. 23, 1995.
[51] Int. Cl.$^6$ .................................................. C07H 17/00
[52] U.S. Cl. ............................................................. 536/23.7
[58] Field of Search ..................... 536/23.7, 24.1, 536/24.2; 435/64.8, 69.1, 69.3, 252.3, 320.1

[56] References Cited

U.S. PATENT DOCUMENTS 5,395,764  3/1995  Riboli et al. .......................... 435/252.5
5,439,810  8/1995  Loosmore et al. ...................... 435/69.3

FOREIGN PATENT DOCUMENTS 0368819   5/1990   European Pat. Off. .
453216   10/1991   European Pat. Off. .
523976    1/1993   European Pat. Off. .

OTHER PUBLICATIONS

Zealey et al 1992 Appl. Environ. Microbiol 58(1): 208–214.
Li et al 1992 J Gen Microbiol 138: 1697–1705.
Kurosky et al 1977 J Biol. Chem 252(20): 7257–7264.
Gross et al 1992 Res Microbiol. 143: 671–687.
Dams et al 1991 Biochimica et Biophysica Acta 1090: 139–141.
Scarlato et al 1991 Mol. Microbiol 5(10) 2493–2498.
Li et al 1991 Mol. Microbiol 5(2) 409–417.
Stibitz et al 1986 Gene 50: 133–140.
Bennetzen et al 1982 J Biol Chem 257(6): 3026–3031.
Goodey et al 1986 Mol Gen Genet 204: 505–511.
Johnson and Burns. 1994. J. Bacterial. 176: 5350.
Locht et al. 1992. EMBO J. 11: 3175.
Zealey et al. 1992. Appl. Environ. Microbiol. 58: 208.
Burnette. 1994. Structure 2: 151.
Holmgren et al. 1993. Vaccine 11: 1179.
Wu and Russell. 1994. Vaccine 12: 215.
Dertzbough and Elson. 1993. Infect. Immun. 61: 384.
Cardenas and Clement. 1993. Vaccine 11: 126.
Airaksinen et al. 1991. Biotechnology Lett 13: 305.
Lebens et al. 1993. Bio/Technology 11: 1574.
Burnette et al. 1991. Infect. Immun. 59: 4266.
Klauser et al. 1990. EMBO J. 1991.
Nicosia et al. 1986. Proc. Natl. Acad. Sci. (USA) 83: 4631.
Loosmore et al. 1989. Nucleic Acid. Res. 17: 8365.
Relman et al. 1989. Proc. Natl. Acad. Sci. (USA) 86: 2637.
Charles et al. 1989. Proc. Natl. Acad. Sci. (USA) 86: 3554.
Dams et al. 1991. Biochen. Biophys. Acta. 1090: 139.
Zealey et al. 1990. Bio/Technology 8: 1025.
Imaizumi et al. 1983. Infect. Immun. 41: 1138.
Nicosia et al. 1987. Infect. Immun. 55: 963.
Makoff et al. 1990. Bio/Technology 8: 1030.
Domenighimi et al. 1990. Molec. Microbiol. 4; 787.
Watson, M. 1984. Nucl. Acids. Res. 12: 5145.

*Primary Examiner*—Karen Carlson
*Attorney, Agent, or Firm*—Sim & McBurney

[57] ABSTRACT

An expression system for expressing gene products from recombinant Bordetella strains and specific nucleic acid molecules useful in transforming Bordetella strains for such expression are described. A nucleic acid molecule may comprise a Bordetella promoter operatively coupled to a heterologous gene encoding a non-Bordetella gene product with the heterologous gene transcriptionally regulated by the Bordetella promoter. The nucleic acid molecule may further comprise a further nucleic acid molecule encoding a leader sequence for secretion of the non-Bordetella gene product. Another nucleic acid molecule may comprise a Bordetella promoter coupled to a nucleic acid sequence encoding a non-Bordetella leader sequence for secretion of a gene product, which may be a Bordetella gene product or a non-Bordetella gene product.

1 Claim, 15 Drawing Sheets

```
Thr Pro Gln Asn Ile Thr Asp Leu Cys Ala Glu Tyr His Asn Thr Gln
ACC CCG CAG AAC ATC ACC GAC CTG TGC GCC GAA TAC CAC AAC ACC CAG

Ile His Thr Leu Asn Asp Lys Ile Phe Ser Tyr Thr Glu Ser Leu Ala
ATC CAT ACC CTG AAC GAC AAG ATC TTC AGC TAC ACC GAA AGC CTG GCC

Gly Lys Arg Glu Met Ala Ile Ile Thr Phe Lys Asn Gly Ala Thr Phe
GGC AAG CGC GAA ATG GCC ATC ATC ACC TTC AAG AAC GGC GCC ACC TTC

Gln Val Glu Val Pro Gly Ser Gln His Ile Asp Ser Gln Lys Lys Ala
CAG GTC GAA GTC CCG GGC AGC CAG CAT ATC GAC AGC CAG AAG AAG GCC

Ile Glu Arg Met Lys Asp Thr Leu Arg Ile Ala Tyr Leu Thr Glu Ala
ATC GAA CGC ATG AAG GAC ACC CTG CGC ATC GCC TAC CTG ACC GAA GCC

Lys Val Glu Lys Leu Cys Val Trp Asn Asn Lys Thr Pro His Ala Ile
AAG GTC GAA AAG CTG TGC GTC TGG AAC AAC AAG ACC CCG CAT GCC ATC

Ala Ala Ile Ser Met Ala Asn ***
GCC GCC ATC AGC ATG GCC AAC TAA
```

FIG.1.

CGGTCACCGT CCGGACCGTG CTGACCCCCC TGCCATGGTG TGATCCGTAA AATAGGCACC ATCAAAACGC AGAGG
GGAAGACGGG ATGATCAAGA TCAAGTTCGG CGTCTTCTTC ACCGTCCTGC TGAGCTCCGC CTACGCCC

ATGGCACCCC GCAGAACATC ACCGACCTGT GCGCCGAATA CCACAACACC CAGATCCATA CCCTGAACGA CAA

GATCTTCAGC TACACCGAAA GCCTGGCCGG CAAGGCGCAA ATGGCCATCA TCACCTTCAA GAA

CGGCGCCACC TTCCAGGTCG AAGTCCCGGG CAGCCAGCAT ATCGACAGCC AGAAGAA

GGCCATCGAA CGCATGAAGG ACACCCTGCG CTGACCGAAG CCAAGGTCGA AAA

GCTGTGCGTC TGGAACAACA AGACCCCGCA TGCCATCGCC GCCATCAGCA TGGCCAACTA AGGATCCG

AATTCGGATC CTTAGTTGGC CATGCTGATG GCGGGCGATGG CATGCGGGGT CTTGTTGTTC CA

GACGCACAGC TTTTCGACCT TGGCTTCGGT CAGGTAGGCG ATGCGCAGGG TGTCCTTCAT GCGTT

CGATGGCCTT CTTCTGGCTG TCGATATGCT GGCTGCCCGG GACTTCGACC TGGAA

GGTGGCGCCG TTCTTGAAGG TGATGATGGC CATTTCGCGC TTGCCGGCCA GGCTTTCGGT GTAGCTGAA

GATCTTGTCG TTCAGGGTAT GGATCTGGGT GTTGTGGTAT TCGGCGCACA GGTCGGTGAT GTTCTGCGGG GTGCCATGGG
CGTAGGC

GGAGCTCAGC AGGACGGTGA AGAAGACGCC GAACTTGATC TTGATCATCC CGTCTTCCCC TCTGCG

TTTTGATGGT GCCTATTTTA CGGATCACAC CATGGCAGGG GGTCAGCAC GGTCCGGACG GTGACCGGTA C

FIG. 3.

```
ATTCTGCCGA TTACTTCACT TCGCTGGTCG GAATATGATC AAGATC
AAGTTCGGCG TCTTCTTCAC CGTCCTGCTG AGCT
CAGCAGGACG GTGAAGAAGA CGCCGAACTT GATCTTGATC
ATATTCCGAC CAGCGAAGTG AAGTAATCGG CAG
```

FIG. 5.

```
CGGTCACCGT CCGGACCGTG CTGACCCCCC TGCCATGGTG TGATCCGTAA AATAGGCACC ATCAAAACGC AGAGG

GGAAGACGGG ATCGTTGC

ACTCGGGCAA TTCGCCAAAC CGCAAGAACA GGCTGGCTGA CGTGGCTGGC G

ATTCTTGCCG TCACGGCGCC CGTGACTTCG CCGGCATGGG CCACCCCGCA G

AACATCACCG ACCTGTGCGC CGAATACCAC AACACCCAGA TCCATACCCT GAACGACAA

GATCTTGTCG TTCAGGGTAT GGATCTGGGT GTTGTGGTAT TCGGCGCACA GGTCGGTGAT GTTCTGCGGG GT

GGCCCATGCC GGCGAAGTCA CGGGCGCCTG ACGGCAAGAA TCGCCAAGCC

ACGTCAGCCA GCCTGTTCTT GCGGTTTGGC GAATTGCCCG AGTGCAACGC AT

CCCGTCTTCC CCTCTGCG

TTTGATGGT GCCTATTTTA CGGATCACAC CATGGCAGGG GGGTCAGCAC GGTCCGGACG GTGACCGGTA C
```

FIG.7.

```
CGGTCACCGT CCGGACCGTG CTGACCCCCC TGCCATGGTG TGATCCGTAA AATAGGCACC ATCAAAACGC AGAGG
GGAAGACGGG ATGAACATG
TCTCTGTCAC GCATTGTCAA GGCGGGCGCCC CTGCGCCCGCA C
CACGCTGGCC ATGGGGCTGG GCGCGCTGGG CGCCGCCCCG GCGGGCGCATG CCACCCCGCA G
AACATCACCG ACCTGTGCGC CGAATACCAC AACACCCAGA TCCATACCCT GAACGACAA
GATCTTGTCG TTCAGGGTAT GTTGTGGTAT TCGGGCGCACA GGTCGGTGAT GTTCTGCGGG GT
GGCATGCGCC GCCGGGGGCG GCCCCAGCGC ATGGCCAGCG TGGTGCGGCG C
AGGGGCGCCG CCTTGACAAT GCGTGACAGA GACATGTTCA T
CCCGTCTTCC CCTCTGCG
TTTTGATGGT GCCTATTTTA CGGATCACAC CATGGCCAGGG GGGTCAGCAC GGTCCGGACG GTGACCGGTA C
```

FIG.9.

```
ATTCTGCCGA  TTACTTCACT  TCGCTGGTCG  GAATATGCTT  GC
ACTCGGGCAA  TTCGCCAAAC  CGCAAGAACA  GGCTGGCTGA  CGTGGCTGGC  G
ATTCTTGCCG  TCACGGCGCC  CGTGACTTCG  CCCGGCATGGG  CCACCCCGCA  G
AACATCACCG  ACCTGTGCGC  CGAATACCAC  AACACCCAGA  TCCATACCCT  GAACGACAA
GATCTTGTCG  TTCAGGGTAT  GGATCTGGGT  GTTGTGGGTAT  TCGGCGCCACA  GGTCGGGTGAT  GTTCTGCGGG  GT
GGCCCATGCC  GGCGAAGTCA  CGGGCGCCGT  GACGGCAAGA  ATCGCCAGCC
ACGTCAGCCA  GCCTGTTCTT  GCGGTTTGGC  GAATTGCCCG  AGTGCAACGC  AT
ATTCCGACCA  GCGAAGTGAA  GTAATCGGCA  G
```

FIG.11.

```
ATTCTGCCGA TTACTTCACT TCGCTGGTCG GAATATGAAC ATG
TCTCTGTCAC GCATTGTCAA GGCGGCGCCC CTGCGCCGCA C
CACGCTGGCC ATGGCGCTGG GCGCGGCTGG CGCCGCCCCG GCGGCGCATG CCACCCCGCA G
AACATCACCG ACCTGTGCGC CGAATACCAGA AACACCCAGA TCCATACCCT GAACGACAA
GATCTTGTCG TTCAGGGTAT GGATCTGGGT GTTGTGGTAT TCGGCGCACA GGTCGGTGAT GTTCTGCGGG C
GGCATGCGCC GCCGGGGCGG CGCCCAGCGC GCCCAGCGCC ATGGCCAGCG TGGTGCGGCG C
AGGGGCGCCG CCTTGACAAT GCGTGACAGA GACATGTTCA T
ATTCCGACCA GCGAAGTGAA GTAATCGGCA G
```

FIG.13.

*fha* locus
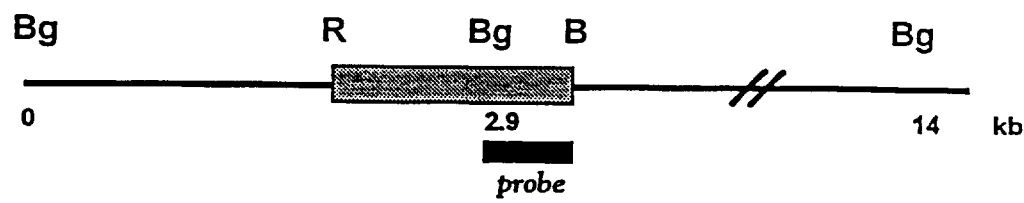
*tox* locus
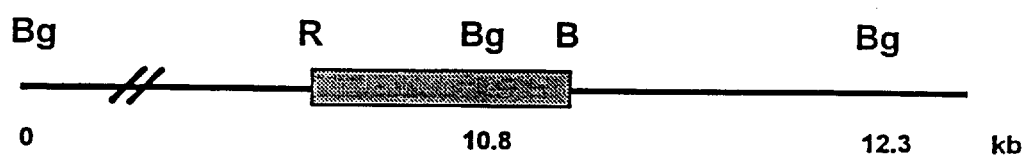
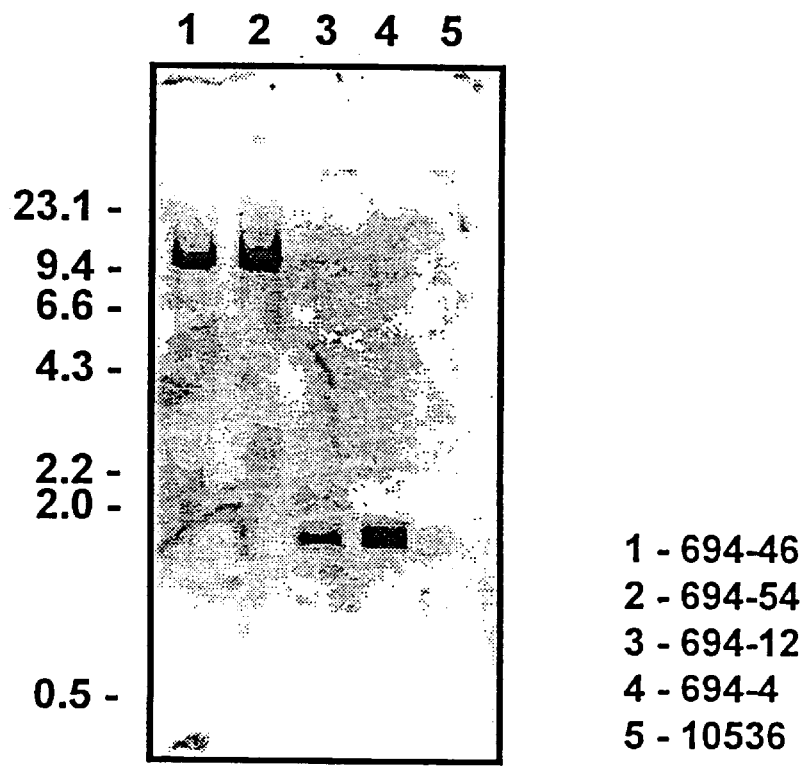
1 - 694-46
2 - 694-54
3 - 694-12
4 - 694-4
5 - 10536
FIG. 14

SDS-PAGE (17.5%)
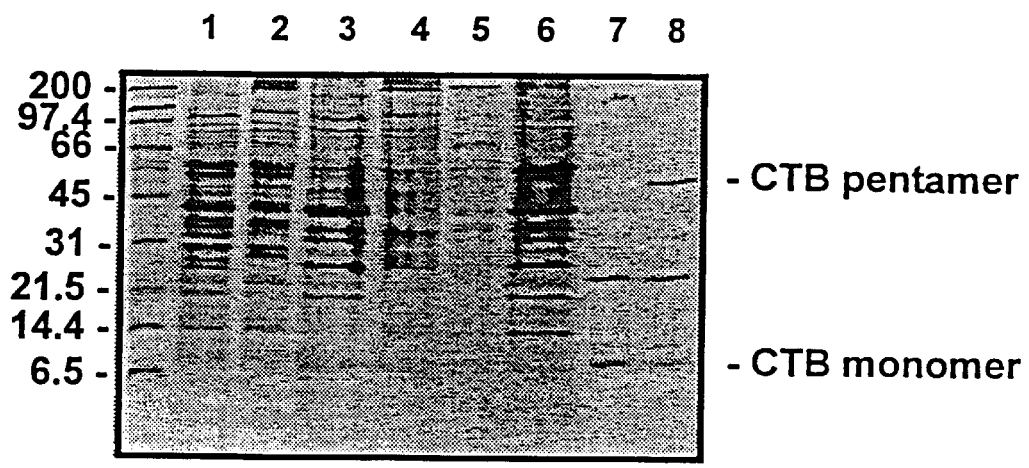
Western Blot
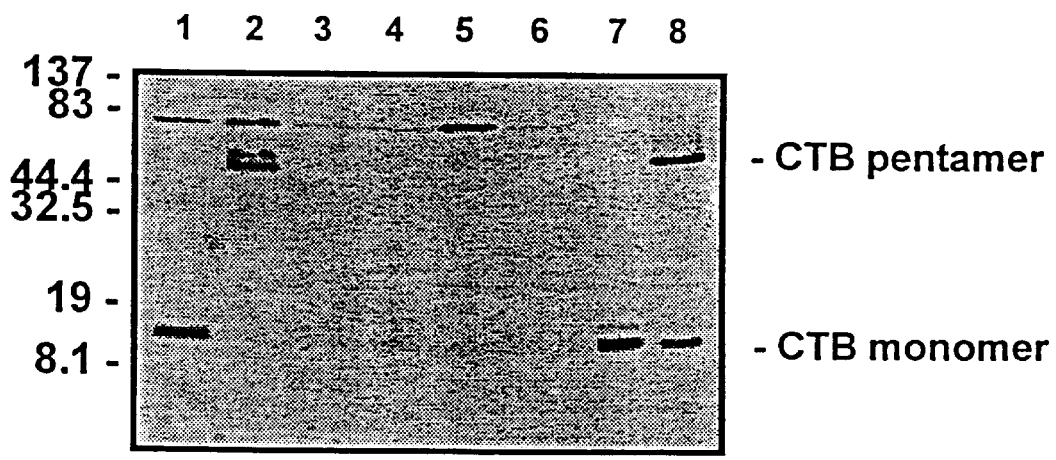
FIG. 15

SEQUENCE LISTING (1) GENERAL INFORMATION:

(iii) NUMBER OF SEQUENCES: 56

(2) INFORMATION FOR SEQ ID NO:1:

(i) SEQUENCE CHARACTERISTICS:
      (A) LENGTH: 312 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 1..309

(xi) SEQUENCE DESCRIPTION: SEQ ID NO:1:

```
ACC CCG CAG AAC ATC ACC GAC CTG TGC GCC GAA TAC CAC AAC ACC CAG         48
Thr Pro Gln Asn Ile Thr Asp Leu Cys Ala Glu Tyr His Asn Thr Gln
 1               5                  10                  15

ATC CAT ACC CTG AAC GAC AAG ATC TTC AGC TAC ACC GAA AGC CTG GCC         96
Ile His Thr Leu Asn Asp Lys Ile Phe Ser Tyr Thr Glu Ser Leu Ala
                20                  25                  30

GGC AAG CGC GAA ATG GCC ATC ATC ACC TTC AAG AAC GGC GCC ACC TTC        144
Gly Lys Arg Glu Met Ala Ile Ile Thr Phe Lys Asn Gly Ala Thr Phe
        35                  40                  45

CAG GTC GAA GTC CCG GGC AGC CAG CAT ATC GAC AGC CAG AAG AAG GCC        192
Gln Val Glu Val Pro Gly Ser Gln His Ile Asp Ser Gln Lys Lys Ala
    50                  55                  60

ATC GAA CGC ATG AAG GAC ACC CTG CGC ATC GCC TAC CTG ACC GAA GCC        240
Ile Glu Arg Met Lys Asp Thr Leu Arg Ile Ala Tyr Leu Thr Glu Ala
65                  70                  75                  80

AAG GTC GAA AAG CTG TGC GTC TGG AAC AAC AAG ACC CCG CAT GCC ATC        288
Lys Val Glu Lys Leu Cys Val Trp Asn Asn Lys Thr Pro His Ala Ile
                85                  90                  95

GCC GCC ATC AGC ATG GCC AAC TAA                                        312
Ala Ala Ile Ser Met Ala Asn
               100
```

(2) INFORMATION FOR SEQ ID NO:2:

(i) SEQUENCE CHARACTERISTICS:
      (A) LENGTH: 103 amino acids
      (B) TYPE: amino acid
      (D) TOPOLOGY: linear (ii) MOLECULE TYPE: protein (xi) SEQUENCE DESCRIPTION: SEQ ID NO:2:

```
Thr Pro Gln Asn Ile Thr Asp Leu Cys Ala Glu Tyr His Asn Thr Gln
 1               5                  10                  15

Ile His Thr Leu Asn Asp Lys Ile Phe Ser Tyr Thr Glu Ser Leu Ala
                20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95
```

Ala Ala Ile Ser Met Ala Asn
            100

(2) INFORMATION FOR SEQ ID NO:3:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:3:

CGGTCACCGT CCGGACCGTG CTGACCCCCC TGCCATGGTG TGATCCGTAA AATAGGCACC        60

ATCAAAACGC AGAGG        75

(2) INFORMATION FOR SEQ ID NO:4:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO:4:

GGAAGACGGG ATGATCAAGA TCAAGTTCGG CGTCTTCTTC ACCGTCCTGC TGAGCTCCGC        60

CTACGCCC        68

(2) INFORMATION FOR SEQ ID NO:5:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:5:

ATGGCACCCC GCAGAACATC ACCGACCTGT GCGCCGAATA CCACAACACC CAGATCCATA        60

CCCTGAACGA CAA        73

(2) INFORMATION FOR SEQ ID NO:6:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (xi) SEQUENCE DESCRIPTION: SEQ ID NO:6:

GATCTTCAGC TACACCGAAA GCCTGGCCGG CAAGCGCGAA ATGGCCATCA TCACCTTCAA        60

GAA        63

(2) INFORMATION FOR SEQ ID NO:7:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:7:

CGGCGCCACC TTCCAGGTCG AAGTCCCGGG CAGCCAGCAT ATCGACAGCC AGAAGAA        57

(2) INFORMATION FOR SEQ ID NO:8:

(i) SEQUENCE CHARACTERISTICS:

(A) LENGTH: 63 base pairs
        (B) TYPE: nucleic acid
        (C) STRANDEDNESS: single
        (D) TOPOLOGY: linear (xi) SEQUENCE DESCRIPTION: SEQ ID NO:8:

GGCCATCGAA CGCATGAAGG ACACCCTGCG CATCGCCTAC CTGACCGAAG CCAAGGTCGA    60

AAA    63

(2) INFORMATION FOR SEQ ID NO:9:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO:9:

GCTGTGCGTC TGGAACAACA AGACCCCGCA TGCCATCGCC GCCATCAGCA TGGCCAACTA    60

AGGATCCG    68

(2) INFORMATION FOR SEQ ID NO:10:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (xi) SEQUENCE DESCRIPTION: SEQ ID NO:10:

AATTCGGATC CTTAGTTGGC CATGCTGATG GCGGCGATGG CATGCGGGGT CTTGTTGTTC    60

CA    62

(2) INFORMATION FOR SEQ ID NO:11:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (xi) SEQUENCE DESCRIPTION: SEQ ID NO:11:

GACGCACAGC TTTTCGACCT TGGCTTCGGT CAGGTAGGCG ATGCGCAGGG TGTCCTTCAT    60

GCGTT    65

(2) INFORMATION FOR SEQ ID NO:12:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (xi) SEQUENCE DESCRIPTION: SEQ ID NO:12:

CGATGGCCTT CTTCTGGCTG TCGATATGCT GGCTGCCCGG GACTTCGACC TGGAA    55

(2) INFORMATION FOR SEQ ID NO:13:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:13:

```
GGTGGCGCCG TTCTTGAAGG TGATGATGGC CATTTCGCGC TTGCCGGCCA GGCTTTCGGT    60

GTAGCTGAA                                                            69
```

(2) INFORMATION FOR SEQ ID NO:14:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (xi) SEQUENCE DESCRIPTION: SEQ ID NO:14:

```
GATCTTGTCG TTCAGGGTAT GGATCTGGGT GTTGTGGTAT TCGGCGCACA GGTCGGTGAT    60

GTTCTGCGGG GTGCCATGGG CGTAGGC                                        87
```

(2) INFORMATION FOR SEQ ID NO:15:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (xi) SEQUENCE DESCRIPTION: SEQ ID NO:15:

```
GGAGCTCAGC AGGACGGTGA AGAAGACGCC GAACTTGATC TTGATCATCC CGTCTTCCCC    60

TCTGCG                                                               66
```

(2) INFORMATION FOR SEQ ID NO:16:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:16:

```
TTTTGATGGT GCCTATTTTA CGGATCACAC CATGGCAGGG GGGTCAGCAC GGTCCGGACG    60

GTGACCGGTA C                                                         71
```

(2) INFORMATION FOR SEQ ID NO:17:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:17:

```
ATTCTGCCGA TTACTTCACT TCGCTGGTCG GAATATGATC AAGATC                   46
```

(2) INFORMATION FOR SEQ ID NO:18:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:18:

```
AAGTTCGGCG TCTTCTTCAC CGTCCTGCTG AGCT                                34
```

(2) INFORMATION FOR SEQ ID NO:19:

(i) SEQUENCE CHARACTERISTICS:
        (A) LENGTH: 40 base pairs (B) TYPE: nucleic acid
        (C) STRANDEDNESS: single
        (D) TOPOLOGY: linear (xi) SEQUENCE DESCRIPTION: SEQ ID NO:19:

CAGCAGGACG GTGAAGAAGA CGCCGAACTT GATCTTGATC                40

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:20:

ATATTCCGAC CAGCGAAGTG AAGTAATCGG CAG                       33

(2) INFORMATION FOR SEQ ID NO:21:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:21:

CGGTCACCGT CCGGACCGTG CTGACCCCCC TGCCATGGTG TGATCCGTAA AATAGGCACC    60

ATCAAAACGC AGAGG                                          75

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:22:

GGAAGACGGG ATCGTTGC                                       18

(2) INFORMATION FOR SEQ ID NO:23:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:23:

ACTCGGGCAA TTCGCCAAAC CGCAAGAACA GGCTGGCTGA CGTGGCTGGC G   51

(2) INFORMATION FOR SEQ ID NO:24:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:24:

ATTCTTGCCG TCACGGCGCC CGTGACTTCG CCGGCATGGG CCACCCCGCA G   51

(2) INFORMATION FOR SEQ ID NO:25:

(i) SEQUENCE CHARACTERISTICS:
        (A) LENGTH: 59 base pairs (B) TYPE: nucleic acid
            (C) STRANDEDNESS: single
            (D) TOPOLOGY: linear (xi) SEQUENCE DESCRIPTION: SEQ ID NO:25:

AACATCACCG ACCTGTGCGC CGAATACCAC AACACCCAGA TCCATACCCT GAACGACAA        59

(2) INFORMATION FOR SEQ ID NO:26:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (xi) SEQUENCE DESCRIPTION: SEQ ID NO:26:

GATCTTGTCG TTCAGGGTAT GGATCTGGGT GTTGTGGTAT TCGGCGCACA GGTCGGTGAT        60

GTTCTGCGGG GT                                                           72

(2) INFORMATION FOR SEQ ID NO:27:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (xi) SEQUENCE DESCRIPTION: SEQ ID NO:27:

GGCCCATGCC GGCGAAGTCA CGGGCGCCTG ACGGCAAGAA TCGCCAAGCC                   50

(2) INFORMATION FOR SEQ ID NO:28:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (xi) SEQUENCE DESCRIPTION: SEQ ID NO:28:

ACGTCAGCCA GCCTGTTCTT GCGGTTTGGC GAATTGCCCG AGTGCAACGC AT                52

(2) INFORMATION FOR SEQ ID NO:29:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:29:

CCCGTCTTCC CCTCTGCG                                                     18

(2) INFORMATION FOR SEQ ID NO:30:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (xi) SEQUENCE DESCRIPTION: SEQ ID NO:30:

TTTTGATGGT GCCTATTTTA CGGATCACAC CATGGCAGGG GGGTCAGCAC GGTCCGGACG        60

GTGACCGGTA C                                                            71

(2) INFORMATION FOR SEQ ID NO:31:

(i) SEQUENCE CHARACTERISTICS:
    (A) LENGTH: 75 base pairs
    (B) TYPE: nucleic acid
    (C) STRANDEDNESS: single
    (D) TOPOLOGY: linear (xi) SEQUENCE DESCRIPTION: SEQ ID NO:31:

CGGTCACCGT CCGGACCGTG CTGACCCCCC TGCCATGGTG TGATCCGTAA AATAGGCACC    60

ATCAAAACGC AGAGG    75

(2) INFORMATION FOR SEQ ID NO:32:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:32:

GGAAGACGGG ATGAACATG    19

(2) INFORMATION FOR SEQ ID NO:33:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:33:

TCTCTGTCAC GCATTGTCAA GGCGGCGCCC CTGCGCCGCA C    41

(2) INFORMATION FOR SEQ ID NO:34:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:34:

CACGCTGGCC ATGGCGCTGG GCGCGCTGGG CGCCGCCCCG GCGGCGCATG CCACCCCGCA    60

G    61

(2) INFORMATION FOR SEQ ID NO:35:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (xi) SEQUENCE DESCRIPTION: SEQ ID NO:35:

AACATCACCG ACCTGTGCGC CGAATACCAC AACACCCAGA TCCATACCCT GAACGACAA    59

(2) INFORMATION FOR SEQ ID NO:36:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:36:

GATCTTGTCG TTCAGGGTAT GGATCTGGGT GTTGTGGTAT TCGGCGCACA GGTCGGTGAT    60

GTTCTGCGGG GT    72

(2) INFORMATION FOR SEQ ID NO:37:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:37:

```
GGCATGCGCC GCCGGGGCGG CGCCCAGCGC GCCCAGCGCC ATGGCCAGCG TGGTGCGGCG     60
C                                                                    61
```

(2) INFORMATION FOR SEQ ID NO:38:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:38:

```
AGGGGCGCCG CCTTGACAAT GCGTGACAGA GACATGTTCA T                        41
```

(2) INFORMATION FOR SEQ ID NO:39:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:39:

```
CCCGTCTTCC CCTCTGCG                                                  18
```

(2) INFORMATION FOR SEQ ID NO:40:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:40:

```
TTTTGATGGT GCCTATTTTA CGGATCACAC CATGGCAGGG GGGTCAGCAC GGTCCGGACG     60
GTGACCGGTA C                                                         71
```

(2) INFORMATION FOR SEQ ID NO:41:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:41:

```
ATTCTGCCGA TTACTTCACT TCGCTGGTCG GAATATGCTT GC                       42
```

(2) INFORMATION FOR SEQ ID NO:42:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:42:

ACTCGGGCAA TTCGCCAAAC CGCAAGAACA GGCTGGCTGA CGTGGCTGGC G        51

(2) INFORMATION FOR SEQ ID NO:43:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:43:

ATTCTTGCCG TCACGGCGCC CGTGACTTCG CCGGCATGGG CCACCCCGCA G        51

(2) INFORMATION FOR SEQ ID NO:44:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (xi) SEQUENCE DESCRIPTION: SEQ ID NO:44:

AACATCACCG ACCTGTGCGC CGAATACCAC AACACCCAGA TCCATACCCT GAACGACAA        59

(2) INFORMATION FOR SEQ ID NO:45:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:45:

GATCTTGTCG TTCAGGGTAT GGATCTGGGT GTTGTGGTAT TCGGCGCACA GGTCGGTGAT        60

GTTCTGCGGG GT        72

(2) INFORMATION FOR SEQ ID NO:46:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:46:

GGCCCATGCC GGCGAAGTCA CGGGCGCCGT GACGGCAAGA ATCGCCAGCC        50

(2) INFORMATION FOR SEQ ID NO:47:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO:47:

ACGTCAGCCA GCCTGTTCTT GCGGTTTGGC GAATTGCCCG AGTGCAACGC AT        52

(2) INFORMATION FOR SEQ ID NO:48:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:48:

ATTCCGACCA GCGAAGTGAA GTAATCGGCA G                          31

(2) INFORMATION FOR SEQ ID NO:49:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:49:

ATTCTGCCGA TTACTTCACT TCGCTGGTCG GAATATGAAC ATG              43

(2) INFORMATION FOR SEQ ID NO:50:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:50:

TCTCTGTCAC GCATTGTCAA GGCGGCGCCC CTGCGCCGCA C                41

(2) INFORMATION FOR SEQ ID NO:51:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:51:

CACGCTGGCC ATGGCGCTGG GCGCGCTGGG CGCCGCCCCG GCGGCGCATG CCACCCCGCA  60

G                                                                  61

(2) INFORMATION FOR SEQ ID NO:52:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (xi) SEQUENCE DESCRIPTION: SEQ ID NO:52:

AACATCACCG ACCTGTGCGC CGAATACCAC AACACCCAGA TCCATACCCT GAACGACAA   59

(2) INFORMATION FOR SEQ ID NO:53:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:53:

GATCTTGTCG TTCAGGGTAT GGATCTGGGT GTTGTGGTAT TCGGCGCACA GGTCGGTGAT  60

GTTCTGCGGG GT                                                      72

(2) INFORMATION FOR SEQ ID NO:54:

(i) SEQUENCE CHARACTERISTICS:
        (A) LENGTH: 61 base pairs
        (B) TYPE: nucleic acid
        (C) STRANDEDNESS: single
        (D) TOPOLOGY: linear -continued (xi) SEQUENCE DESCRIPTION: SEQ ID NO:54:

GGCATGCGCC GCCGGGGCGG CGCCCAGCGC GCCCAGCGCC ATGGCCAGCG TGGTGCGGCG      60

C      61

(2) INFORMATION FOR SEQ ID NO:55:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:55:

AGGGGCGCCG CCTTGACAAT GCGTGACAGA GACATGTTCA T      41

(2) INFORMATION FOR SEQ ID NO:56:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:56:

ATTCCGACCA GCGAAGTGAA GTAATCGGCA G      31

EXPRESSION OF GENE PRODUCTS FROM GENETICALLY MANIPULATED STRAINS OF BORDETELLA

This is a continuation of application Ser. No. 08/393,334 filed Feb. 23, 1995.

FIELD OF THE INVENTION

The present invention relates to the field of molecular biology and is particularly concerned with the expression of gene products from strains of Bordetella.

BACKGROUND OF THE INVENTION

*Bordetella pertussis*, the organism responsible for whooping cough, expresses a number of virulence factors, such as pertussis toxin (PT), filamentous hemagglutinin (FHA) and pertactin (PRN). These proteins are secreted by the organism through the use of signal peptides and/or accessory genes (refs. 1 and 2—Throughout this specification, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure). We have previously demonstrated that it is possible to manipulate the expression of these Bordetella proteins through alteration of gene copy number (ref. 3) or the use of hybrid genes with autologous promoters (ref. 4). For example, the amount of secreted and processed PT holotoxin was increased more than 3-fold by increasing the copy number of the tox operon encoding PT (ref. 5). The amount of secreted and processed pertactin was increased 8-fold by using a hybrid gene which replaced the native prn promoter with the stronger fha promoter. The yield of pertactin was further increased to 20-fold wild-type levels by adding a second copy of the hybrid gene.

Many gene products including proteins and polypeptides of commercial and medical significance are only available in small amounts from their natural sources, are difficult to isolate or require modification of, for example, their primary amino acid sequence for optional use and/or activity. Thus, many genes have been expressed by recombinant DNA means in a variety of microbial hosts, including bacterial hosts. The gene expressed in the microbial host is typically heterologous to the host.

Examples of bacterial hosts used for expression of heterologous proteins include strains of *Escherichia coli*, Salmonella species (ref. 10) and *Bacillus subtilis* (ref. 11).

Particular biological properties of strains of Bordetella make them attractive hosts for the production of certain heterologous gene products. Thus, many of the antigens produced by *B. pertussis* are large, can be multimeric and may require post-translational assembly or processing. For example, the pertactin antigen is produced as a 93-kDa precursor and the mature protein is produced by excision of the N-terminal signal peptide and removal of a C-terminal fragment. Pertussis toxin is a 105 kDa exotoxin produced by *B. pertussis*, and is encoded by the TOX operon and consists of five polypeptide subunits (S1 to S5) arranged in the typical A-B structure of bacterial toxins. The S2, S3, S4 and S5 subunit form a pentamer (the B oligomer) which, when combined with the S1 subunit forms the holotoxin. For PT, for example, such complex assembly cannot be achieved in *E. coli* (ref. 22) and, for the 69 kd material, protein accumulated as insoluble inclusion bodies in *E. coli* (ref. 23). This intracellular expression in *E. coli* is to be contrasted with the secretion of soluble antigens by *B. pertussis* strains. FHA is another large molecule (Mwt 220 kDa) secreted by *B. pertussis* (ref. 24).

*Vibrio cholerae* is the organism that causes cholera, a severe disease of dehydration caused by diarrhoea. Many of the symptoms of cholera can be attributed to the action of cholera toxin (CT), which like *B. pertussis* PT, is an A/B toxin with ADP-ribosyl transferase activity. However, unlike PT which has four different B subunit components comprising a pentamer, CT has a pentameric structure made up of identical subunits (ref. 6) Cholera toxin has been shown to have considerable use as a mucosal adjuvant and the B subunit alone may be sufficient to generate a mucosal response in some instances (ref. 7). A response is generated if cholera toxin B (CTB) is either co-administered or chemically coupled to another protein (ref. 8). Chimeric genes have also been engineered which have foreign epitopes fused to cholera toxin B and the resultant fusion proteins can sometimes induce an immune response to the foreign epitope (ref. 9).

Cholera toxin B has been expressed from recombinant *V. cholerae* (ref. 12), *E. coli* (ref. 13), and *S. typhimurium* (ref. 14). Although *B. pertussis* has been used to over-express autologous proteins by gene manipulation (refs. 4 and 5), it has not heretofore been used to produce heterologous proteins.

SUMMARY OF THE INVENTION

The present invention is directed towards recombinant strains of Bordetella which express non-Bordetella gene products. Accordingly, in one aspect of the present invention, there is provided a nucleic acid molecule comprising a Bordetella promoter operatively coupled to a heterologous gene encoding a non-Bordetella gene product, wherein the heterologous gene is transcriptionally regulated by the Bordetella promoter.

The non-Bordetella gene product may be one of a wide variety of proteins and polypeptides. The protein or peptide may be an enzyme, an enzyme inhibitor, an antigen, an immunogen, an allergen, a hormone, a lymphokine, an immunoglobulin or fragment thereof, a toxin, a toxin subunit, a mammalian protein, a structural protein or a receptor.

The invention is illustrated by the expression of a cholera toxin -molecule as the non-Bordetella gene product, specifically the B subunit of cholera toxin. However, any other protein or polypeptide may comprise the expressed non-Bordetella gene product.

The Bordetella promoter employed in the nucleic acid molecule provided in accordance with this aspect of the invention may be any of the Bordetella promoters, preferably the tox, prn and fha promoters from any Bordetella strain, including *B. pertussis*.

The heterologous gene component of the nucleic acid molecule provided in accordance with this aspect of the invention may further comprise a nucleic acid sequence encoding a leader sequence for secretion of the non-Bordetella gene product. The leader sequence may be any sequence mediating secretion of the non-Bordetella gene product.

In one embodiment, the leader sequence is a leader sequence of a Bordetella protein or subunit thereof or a fragment or analog of the Bordetella protein leader sequence retaining secretion-mediating properties. The leader sequence may be the Bordetella pertactin leader sequence or a pertussis toxin subunit leader sequence, such as that for the S1 subunit, of any Bordetella strain, including *B. pertussis*.

Alternatively, in another embodiment, the leader sequence is a leader sequence of a non-Bordetella protein or subunit thereof or a fragment or analog of the non-Bordetella protein leader sequence retaining secretion-mediating properties. The non-Bordetella gene product may be a secreted gene product, in which case the non-Bordetella leader sequence preferably is the native leader sequence of the secreted gene product.

In an illustrative example of the latter embodiment of the invention, the secreted gene product may be a cholera toxin molecule, for example, the B subunit thereof and the leader sequence may be the cholera toxin B subunit leader sequence.

Specific combinations of promoter, leader sequence and heterologous gene product sequence are provided herein, including those designed toxp/CTB-L/ctb, fha/CTB-L/ctb, toxp/S1-L/ctb, toxp/PRN-L/ctb, fhap/S1-L/ctb and fha /PRN-L/ctb.

The nucleic acid molecule provided in accordance with this aspect of the invention may further comprise a first DNA sequence corresponding to a 5' flanking sequence of a selected Bordetella gene and disposed at the 5' end of the nucleic acid molecule and a second DNA sequence corresponding to a 3' flanking sequence of the selected Bordetella gene and disposed at the 3' end of the nucleic acid molecule. The first and second DNA sequences permit specific integration of the nucleic acid molecule into the genome of a Bordetella species, preferably *B. pertussis*, at a locus corresponding to the selected Bordetella gene. The Bordetella promoter present in the nucleic acid molecule may be that of the selected Bordetella gene providing the flanking sequences. The selected Bordetella gene may be any of the Bordetella genes, including the tox, prn or fha gene of a Bordetella strain, preferably *B. pertussis*.

The nucleic acid molecule with flanking regions as described above may be provided in a plasmid adapted for transformation of a Bordetella strain, preferably a *B. pertussis* strain. Specific plasmids have been prepared herein, as described in more detail below and are identified as plasmids DS-546-1, JB-898-2-1, DS-729-1-1, DS-729-2-1, JB-1201-4 and JB-1141-5.

Another aspect of the invention provides a recombinant strain of Bordetella, which may be a *B. pertussis* strain, a *B. parapertussis* strain, a *B. bronchiseptica* strain or a *B. avium* strain, particularly a *B. pertussis* strain, containing the nucleic acid molecule provided in the above-described aspect of the invention, integrated into the genome thereof and expressing the non-Bordetella gene product. One specific recombinant *B. pertussis* strain provided herein is *B. pertussis* strain 694-46, which has been deposited with the American Type Culture Collection, Rockville, Md., U.S.A., on Jan. 11, 1995 under the terms of the Budapest Treaty as ATCC Accession number 55,654. The non-Bordetella gene product may be obtained by culturing a recombinant strain provided herein.

In a further aspect of the invention, there is provided a nucleic acid molecule comprising a Bordetella promoter coupled to a nucleic acid sequence encoding a non-Bordetella leader sequence for secretion of a gene product. The secreted gene product may be a Bordetella gene product or a non-Bordetella gene product.

The Bordetella promoter component of the nucleic acid molecule provided in accordance with this further aspect of the invention may be any of the Bordetella promoters, preferably the TOX, PRN or FHA promoter of a Bordetella strain, preferably *B. pertussis*.

The non-Bordetella leader sequence component of the nucleic acid molecule provided in accordance with this further aspect of the invention may be any of the leader sequences mediating secretion of a gene product, including bacterial (prokaryotic) leader sequences (such as *E. coli* leader sequences including rlpB, pal ompA, pilin gene leader sequences and *H. influenzae* leader sequences including the transferrin receptor protein leader sequence), eukaryotic leader sequences (including mammalian) and viral leader sequences. Some appropriate leader sequences for use in aspects of the present invention are described in reference 25. In an illustrative example of this further aspect of the invention, the non-Bordetella leader sequence may be that for the cholera toxin B subunit.

A recombinant strain of Bordetella, such as a *B. pertussis* strain, a *B. parapertussis* strain, *B. bronchiseptica* strain or a *B. avium* strain, preferably a *B. pertussis* strain, may contain the nucleic acid molecule provided in accordance with this further aspect of the invention and secrete --the gene product. Such recombinant strain of Bordetella may be cultured under a range of appropriate conditions to secrete the gene product.

In an additional aspect of the invention, the heterologous gene may be provided with optimized codons for Bordetella expression. One example of such heterologous gene has the nucleic acid sequence of FIG. 1, which encodes the B subunit of cholera toxin and constitutes an embodiment of this additional aspect of the invention.

The present invention, therefore, provides an expression system for expressing gene products from recombinant Bordetella strains and specific nucleic acid molecules useful in transforming Bordetella strains for such expression. The expressed gene products have a variety of uses, depending on the form and nature of the product produced, as will be evident to a person skilled in the art.

BRIEF DESCRIPTION OF THE DRAWINGS

The present invention will be further understood from the following detailed description and examples with reference to the accompanying drawings, in which:

FIG. 1 shows the sequence of a synthetic cholera toxin B subunit gene (SEQ ID NO: 1) and its derived amino acid sequence (SEQ ID NO: 2), based upon strain 569B of *V. cholerae;*

FIG. 3 shows the sequences of oligonucleotides (SEQ ID NOS: 3 to 16) used for the construction of plasmid DS-546-1;

FIG. 5 shows the sequences of oligonucleotides (SEQ ID NOS: 17 to 20) used to construct plasmid JB-898-2-1;

FIG. 7 shows the sequences of oligonucleotides (SEQ ID NOS: 21 to 30) used-to construct plasmid DS-729-1-1;

FIG. 9 shows the sequences of oligonucleotides (SEQ ID NOS: 31 to 40) used to construct plasmid DS-729-2-1;

FIG. 11 shows the sequences of oligonucleotides (SEQ ID NOS: 41 to 48) used to construct plasmid JB-1201-4;

FIG. 13 shows the sequences of oligonucleotides (SEQ ID NOS: 49 to 56) used to construct plasmid JB-1141-5;

FIG. 14 shows the chromosomal maps of the genes at the fha and tox loci and the corresponding Southern blot showing the correct chromosomal integration. Chromosomal DNA was digested with Bgl II and hybridized with the approximately 300 bp ctb probe indicated in the figure. Lane 1, strain 694-46 (fhap/PRN-L/ctb); lane 2, strain 694-54

(fha/S1-L/ctb); lane 3, strain 694-12 (toxp/PRN-L/ctb); lane 4, strain 694-4 (toxp/S1-L/ctb); lane 5, strain 10536 (wild-type *B. pertussis*); and FIG. 15 shows the SDS PAGE and corresponding Western blot of recombinant *B. pertussis* strain 694-46 Which expresses CTB. Lane 1, acetone precipitated supernatant from strain 694-46 (fhap/PRN-L/ctb), boiled in SDS; lane 2, acetone precipitated supernatant from strain 694-46, unboiled; lane 3, cell pellet from strain 694-46, boiled in SDS; lane 4, cell pellet from strain 694-46, unboiled; lane 5, acetone precipitated supernatant from strain 10536 (wild-type *B. pertussis*); lane 6, cell pellet from strain 10536; lane 7, purified cholera toxin (Sigma), boiled in SDS; lane 8, purified cholera toxin, unboiled.

Figure 2:
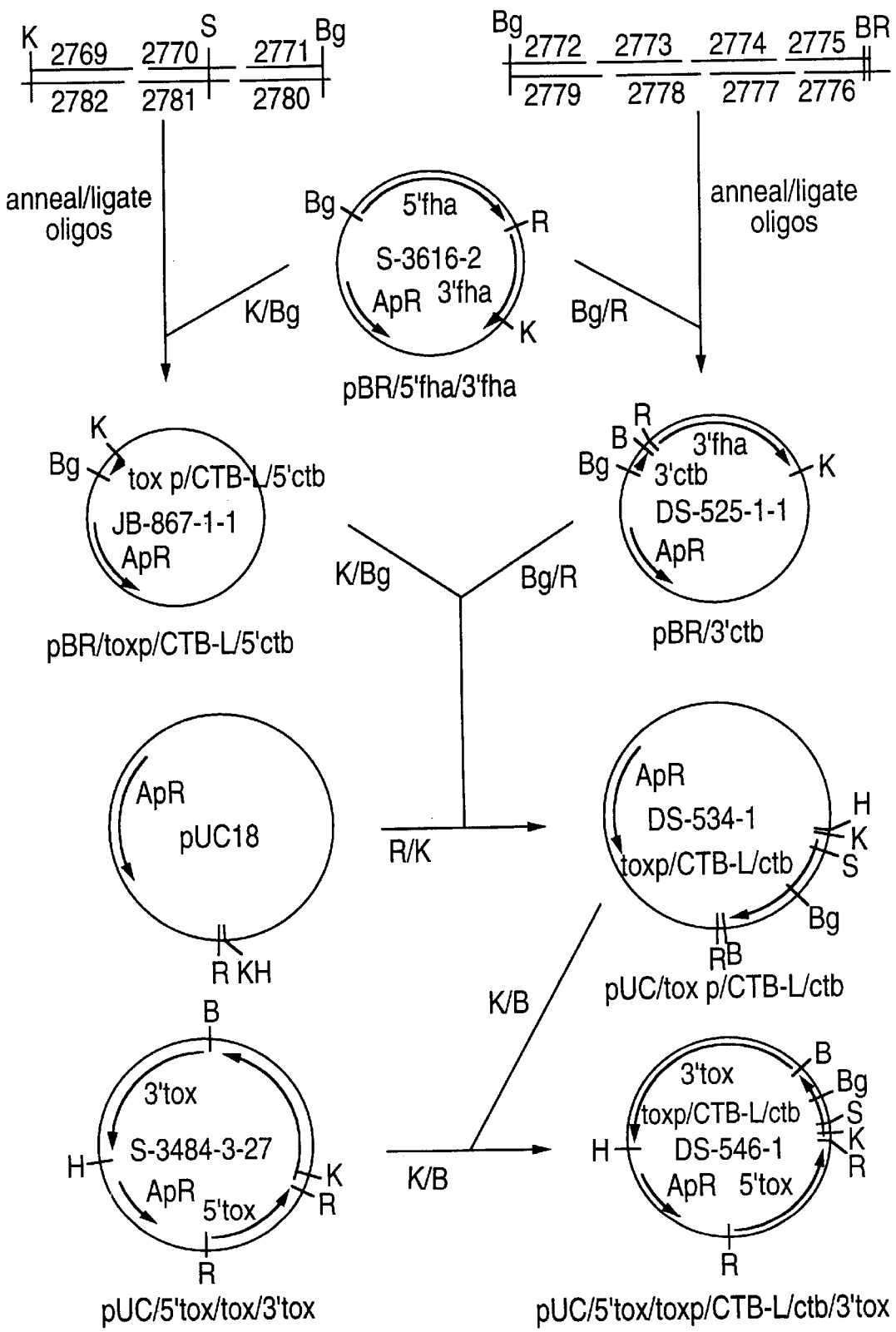
FIG. 2 shows the construction scheme for plasmid DS-546-1 which contains the toxp/CTB-L/ctb gene.

In some of the above figures, the following abbreviations are used:

toxp is the *B. pertussis* tox promoter fhap is the *B. pertussis* fha promoter ctb is the synthetic cholera toxin B gene (SEQ ID NO:1)

CTB-L is the sequence encoding the cholera toxin B subunit leader sequence

S1-L is the sequence encoding the pertussis toxin subunit S1 leader sequence

PRN-L is the sequence encoding the pertussis pertactin leader sequence

Restriction enzyme recognition sites are B, BamH I; Bg, Bgl II; H, Hind III; K, Kpn I; R, EcoR I; S, Sac I; and Hf, HinfI CAP is calf alkaline phosphatase

GENERAL DESCRIPTION OF THE INVENTION

*Bordetella pertussis* 10536 is the vaccine production strain of the assignee hereof and it has been used as the initial strain for all the work detailed by the inventors herein. The genes for *B. pertussis* PT, FHA and pertactin and *V. cholerae* CT have been cloned and sequenced (Refs. 15 to 19) and the promoter regions and transcriptional starts of the structural genes have been determined.

The inventors have generated hybrid genes by substituting the *B. pertussis* native structural genes encoding a leader sequence and/or mature protein by gene segments encoding native, autologous, or heterologous leader peptides and a mature foreign protein. This was accomplished by fusing the promoters with the gene segment encoding the leader peptide at the ATG start codon, followed by the structural gene for the mature foreign protein joined at the natural cleavage site of the signal sequence. Such fusions result in a native promoter, a native, autologous, or heterologous leader peptide, and a heterologous structural gene. The resultant hybrid genes then have been integrated by homologous recombination into the chromosome of *B. pertussis* at the loci corresponding to the gene from which the promoters were derived.

As examples of the use of hybrid genes expressing foreign proteins, genes have been created containing a tox promoter with the cholera toxin B leader peptide and mature cholera toxin B sequence; a tox promoter with the pertussis toxin subunit S1 leader peptide and mature cholera toxin B sequence; a tox promoter with the pertactin leader peptide and mature cholera toxin B sequence; an fha promoter with the cholera toxin B leader peptide and mature cholera toxin B sequence; an fha promoter with the pertussis toxin subunit S1 leader peptide and mature cholera toxin B sequence; and an fha promoter with the pertactin leader peptide and mature cholera toxin B sequence. A number of *B. pertussis* strains have been generated to demonstrate the success of this strategy.

The efficiency of expression of the foreign CTB protein is dependent upon both the promoter and the leader peptide which precede the structural ctb gene. The use of the fha promoter in the hybrid genes results in a higher level of expression of the foreign protein than when the tox promoter is used. This phenomenon was also observed when hybrid genes were used to express. autologous proteins from *B. pertussis* (ref. 4). For the leader peptides, expression levels varied as follows: pertactin>PT subunit S1>cholera toxin B. The best combination of promoter and leader peptide in the hybrid genes expressing foreign proteins was the fha promoter with the pertactin leader peptide.

The CTB expressed by the recombinant *B. pertussis* strains is produced and is a pentamer as demonstrated by SDS PAGE and Western blot analysis of unboiled (pentameric) and boiled (monomeric) samples. The CTB binds to GM1 as demonstrated by ELISA. Thus, a complex foreign protein which has authentic structure and binding function an be secreted by the recombinant Bordetella strains of the invention.

It has been clearly demonstrated that the structural gene of a foreign protein may be fused to a *B. pertussis* promoter through a gene fragment encoding a native, autologous, or heterologous leader peptide to express foreign proteins.

BIOLOGICAL DEPOSITS

*B. pertussis* strain 694-46 which contains the fhap/PRN-L/ctb hybrid gene at the fha locus has been deposited with the American Type Culture Collection (ATCC) located at Rockville, Md., U.S.A., pursuant to the Budapeast Treaty and prior to the filing of this application. The ATCC access number is 55,654.

Samples of the deposited strain will become available to the public upon the grant of a patent based on this United States patent application. The invention described and claimed herein is not limited in scope by the strain deposited, since the deposited embodiment is intended only as an illustration of the invention. Any equivalent or similar strains to that deposited are within the scope of the invention.

EXAMPLES

The above disclosure generally describes the present invention. A more complete understanding can be obtained by reference to the following specific Examples. These Examples are described solely for the purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, and immunology used but not explicitly described in this disclosure and these Examples are amply within the ability of those skilled in the art.

Example 1

This Example illustrates the construction of a synthetic gene encoding the cholera toxin B subunit.

A gene encoding the cholera toxin B subunit was synthesized from a number of oligonucleotides. The oligonucleotides were synthesized on an ABI model 380B DNA synthesizer and purified by gel electrophoresis. Nucleotide sequences were confirmed by automated DNA sequencing on the ABI model 370A DNA sequencer using dye terminator chemistry. For construction of the synthetic gene encoding cholera toxin subunit, codons preferred by *B.*

*pertussis* were selected. The nucleotide sequence of the hybrid gene is shown in FIG. 1 (SEQ ID NO: 1).

Example 2

This Example illustrates the construction of plasmid DS-546-1 containing the toxp/CTB-L/ctb gene.

Oligonucleotides 2769.SL (SEQ ID NO: 3), 2770.SL (SEQ ID NO: 4), 2771.SL (SEQ ID NO: 5), 2780.SL (SEQ ID NO: 14), 2781.SL (SEQ ID NO: 15) and 2782.SL (SEQ ID NO: 16) (FIG. 3) contain part of the tox promoter, encode the cholera toxin B leader peptide, and contain ~70 bp of the 5'-end of the ctb gene encoding the mature cholera toxin B subunit protein. Plasmid S-3616-2 is an 8.6 kb pBR322-based plasmid containing 2.5 kb of the 5'- and 1.3 kb of the 3'-flanking regions for the fha structural gene between Bgl II and Kpn I sites (FIG. 2). Oligonucleotides 2769.SL, 2770.SL, 2771.SL, 2780.SL, 2781.SL, and 2782.SL were kinased, annealed, and ligated with the 4.8 kb vector fragment of S-3616-2 which had been digested with Bgl II and Kpn I to form plasmid JB-867-1-1, which contains a toxp/CTB-L/5'ctb gene insert on a ~220 bp Kpn I/Bgl II fragment.

Oligonucleotides 2772.SL to 2779.SL (SEQ ID NOs: 6 to 13) (see FIG. 3) encode the remaining ~250 bp of the ctb gene. They were kinased, annealed, and ligated with the 6.1 kb vector fragment from plasmid S-3616-2, which had been digested with Bgl II and EcoR I, to generate plasmid DS-525-1-1.

The Kpn I/Bgl II fragment from plasmid JB-867-1-1 and the Bgl II/EcoR I fragment of plasmid DS-525-1-1 were ligated into pUC18, which had been digested with Kpn I and EcoR I, to generate plasmid DS-534-1 which thus contains the entire toxp/CTB-L/ctb gene.

Plasmid S-3484-3-27 is a 14.2 kb pUC-based plasmid containing a mutant tox gene between the 5'- and 3'-tox flanking regions. Digestion with Kpn I and BamH I excised ~4.7 kb of the tox structural gene. The ~470 bp Kpn I/BamH I hybrid gene fragment from DS-534-1 was ligated into the Kpn I/BamH I vector fragment from S-3484-3-27 to generate plasmid DS-546-1 (FIG. 2) which contains the toxp/CTB-L/ctb hybrid gene between the tox flanking regions. This plasmid was used for insertion of the toxp/CTB-L/ctb gene into the tox locus of *B. pertussis*, generating strain 492-320.

Example 3

This Example describes the construction of plasmid JB-898-2-1 containing the fha/CTB-L/ctb gene.

Figure 4:
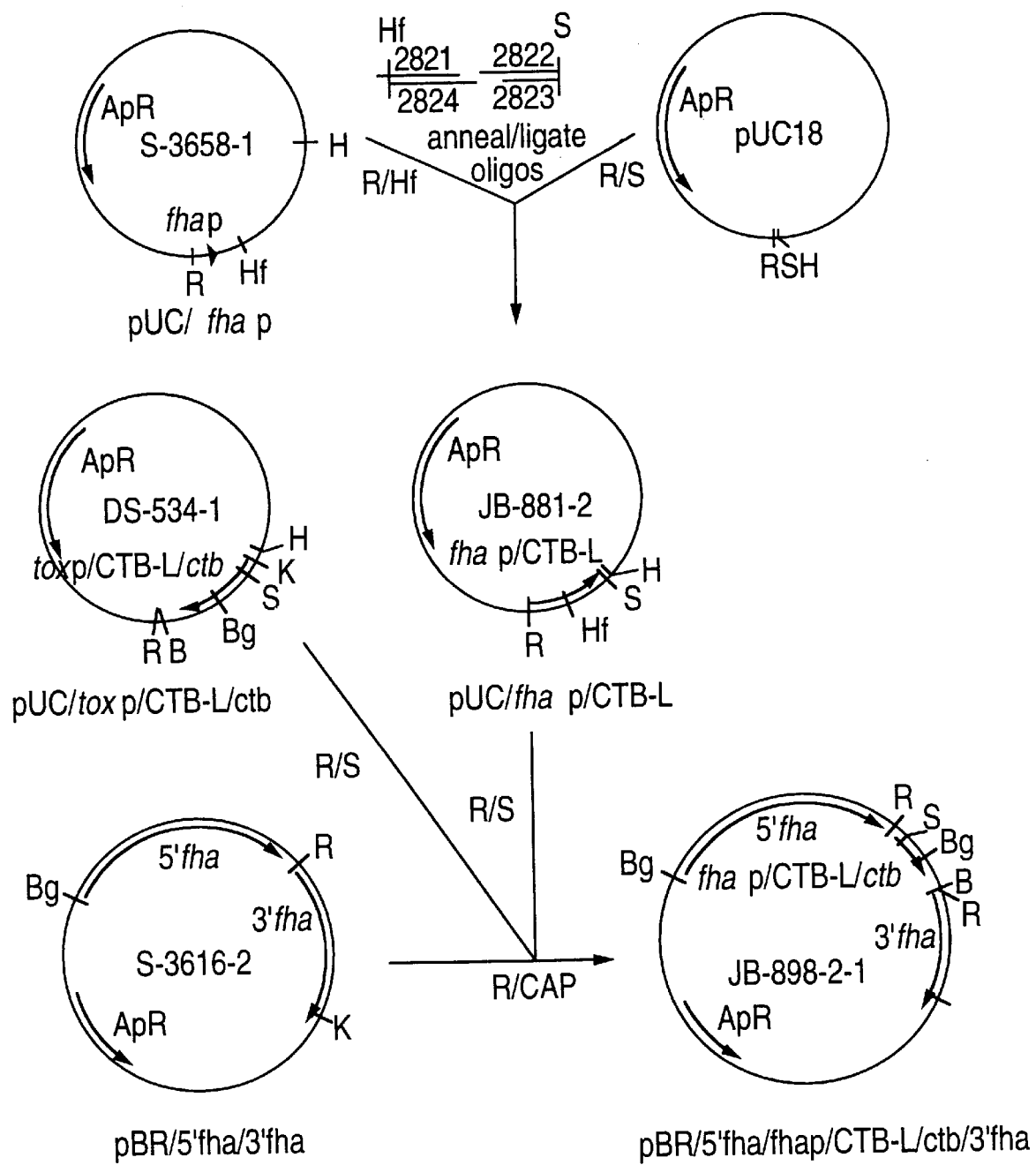
FIG. 4 shows the construction scheme for plasmid JB-898-2-1 which contains the fha/CTB-L/ctb gene.

Plasmid S-3658-1 contains a ~210 bp EcoR I/Hinf I fragment of the fha promoter (FIG. 4). Oligonucleotides 2821.SL to 2824.SL (SEQ ID NOS: 17 to 20) (see FIG. 5) encode the remaining 36 bp of the fha promoter and encode most of the cholera toxin B leader peptide. Oligonucleotides 2821.SL to 2824.SL were kinased, annealed, and ligated with the EcoR I/Hinf I fha promoter fragment from S-3658-1 into pUC18 which had been digested with EcoR I and Sac I. Plasmid JB-881-2 thus contains a portion of the fhap/CTB-L hybrid gene on a 290 bp EcoR I/Sac-I fragment. Digestion of plasmid DS-534-1, which contains the complete toxp/CTB-L/ctb gene, with EcoR I and Sac I excised a ~340 bp fragment of the ctb gene. Ligation of the EcoR I/Sac I fragments from DS-534-1 and JB-881-2 into S-3616-2, which had been digested with EcoR I and dephosphorylated, generated plasmid JB-898-2-1 (FIG. 4) which contains the entire fhap/CTB-L/ctb gene between the fha flanking regions. This plasmid was used to insert the fhap/CTB-L/ctb hybrid gene into the fha locus of *B. pertussis*, generating strain 492-363.

Example 4

This Example illustrates the construction of plasmid DS-729-1-1 which contains the toxp/S1-L/ctb hybrid gene.

Figure 6:
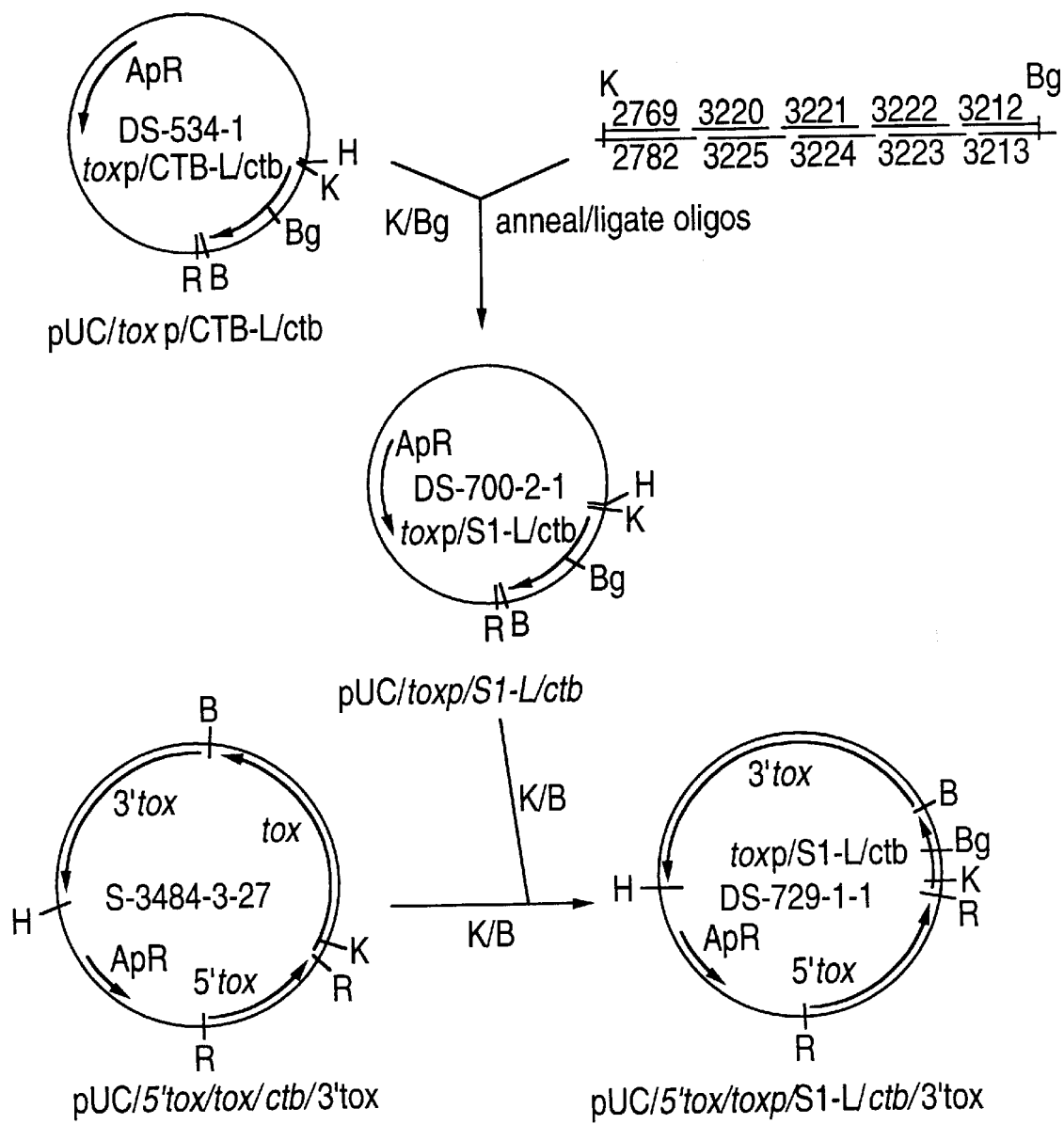
FIG. 6 shows the construction scheme for plasmid DS-729-1-1 which contains the toxp/S1-L/ctb gene.

Plasmid DS-534-1 contains the complete toxp/CTB-L/ctb gene on a ~470 bp Kpn I/EcoR I fragment (FIG. 6). Oligonucleotides 2769.SL (SEQ ID NO: 21), 3220.SL (SEQ ID NO: 22), 3221.SL (SEQ ID NO: 23), 3222.SL (SEQ ID NO: 24), 3212.SL (SEQ ID NO: 25), 2782.SL (SEQ ID NO: 30), 3225.SL (SEQ ID NO: 29), 3224.SL (SEQ ID NO: 28), 3223.SL (SEQ ID NO: 27) and 3213.SL (SEQ ID NO: 26) (see FIG. 7) contain part of the tox promoter, encode the pertussis toxin subunit S1 leader peptide, and contain ~70 bp of the 5'-end of ctb encoding the mature cholera toxin. B subunit protein. The oligonucleotides were kinased, annealed, and ligated with the 3 kb Kpn I/Bgl II vector fragment from DS-534-1 (FIG. 6) to generate plasmid DS-700-2-1 which thus contains the complete toxp/S1-L/ctb gene on a ~505 bp Kpn I/BamH I fragment. The Kpn I/BamH I tox structural gene was excised from plasmid S-3484-3-27 and the toxp/S1-L/ctb gene inserted, to generate plasmid DS-729-1-1 which contains the toxp/S1-L/ctb gene between the tox flanking regions (FIG. 6). This plasmid was used to insert the toxp/S1-L/ctb hybrid gene into the tox. locus of *B. pertussis,* generating strain 694-4.

Example 5

This-Example illustrates the construction of plasmid DS-729-2-1 which contains the toxp/PRN-L/ctb hybrid gene.

Figure 8:
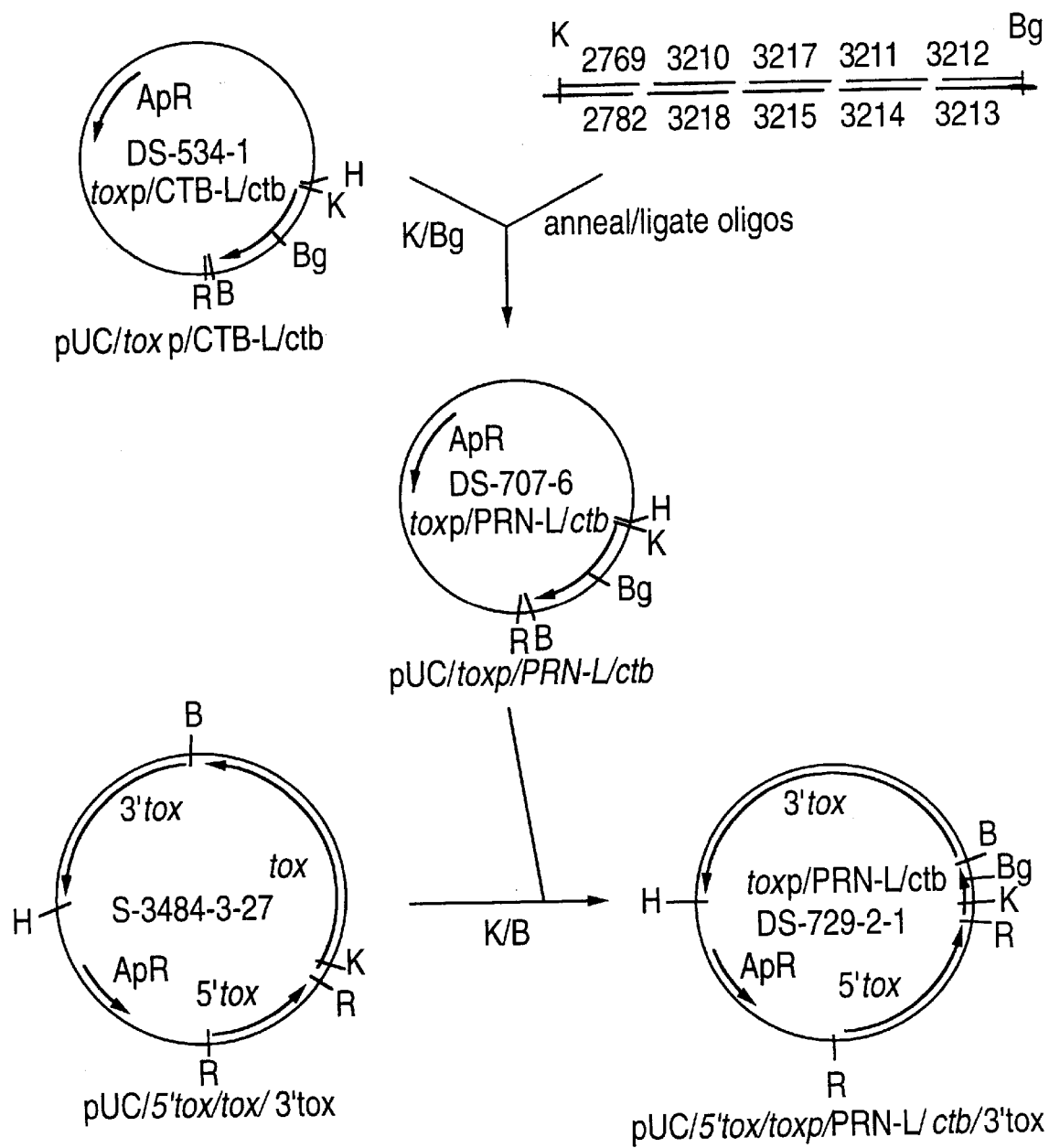
FIG. 8 shows the construction scheme for plasmid DS-729-2-1 which contains the toxp/PRN-L/ctb gene.

Oligonucleotides 2769.SL (SEQ ID NO: 31), 3210.SL (SEQ ID NO: 32), 3217.SL (SEQ ID NO: 33), 3211.SL (SEQ ID NO: 34), 3212.SL (SEQ ID NO: 35), 3213.SL (SEQ ID NO: 36), 3214.SL (SEQ ID NO: 37), 3215.SL (SEQ ID NO: 38), 3218.SL (SEQ ID NO: 39) and 2782.SL (SEQ ID NO: 40) (see FIG. 9) contain part of the tox promoter, encode the pertactin leader peptide, and contain ~70 bp of the ctb gene encoding the mature cholera toxin B subunit protein. The oligonucleotides were kinased, annealed, and ligated into DS-534-1 (FIG. 8) which had been digested with KpnI and Bgl II to delete ~220 bp of the 5'-end of the toxp/CTB-L/ctb hybrid gene (FIG. 5A). Plasmid DS-707-6 contains the complete toxp/PRN-L/ctb hybrid gene on a ~505 bp Kpn I/BamH I fragment. S-3484-3-27 was digested with Kpn I and BamH I to excise the tox structural gene and the hybrid gene was inserted. The resulting plasmid DS-729-2-1 contains the toxp/PRN-L/ctb gene between the tox flanking regions (FIG. 8) and was used for insertion of the hybrid gene into the tox locus of *B. pertussis,* generating strain 694-12.

Example 6

This Example illustrates the construction of plasmid JB-1201-4 which contains the fha/S1-L/ctb hybrid gene.

Figure 10:
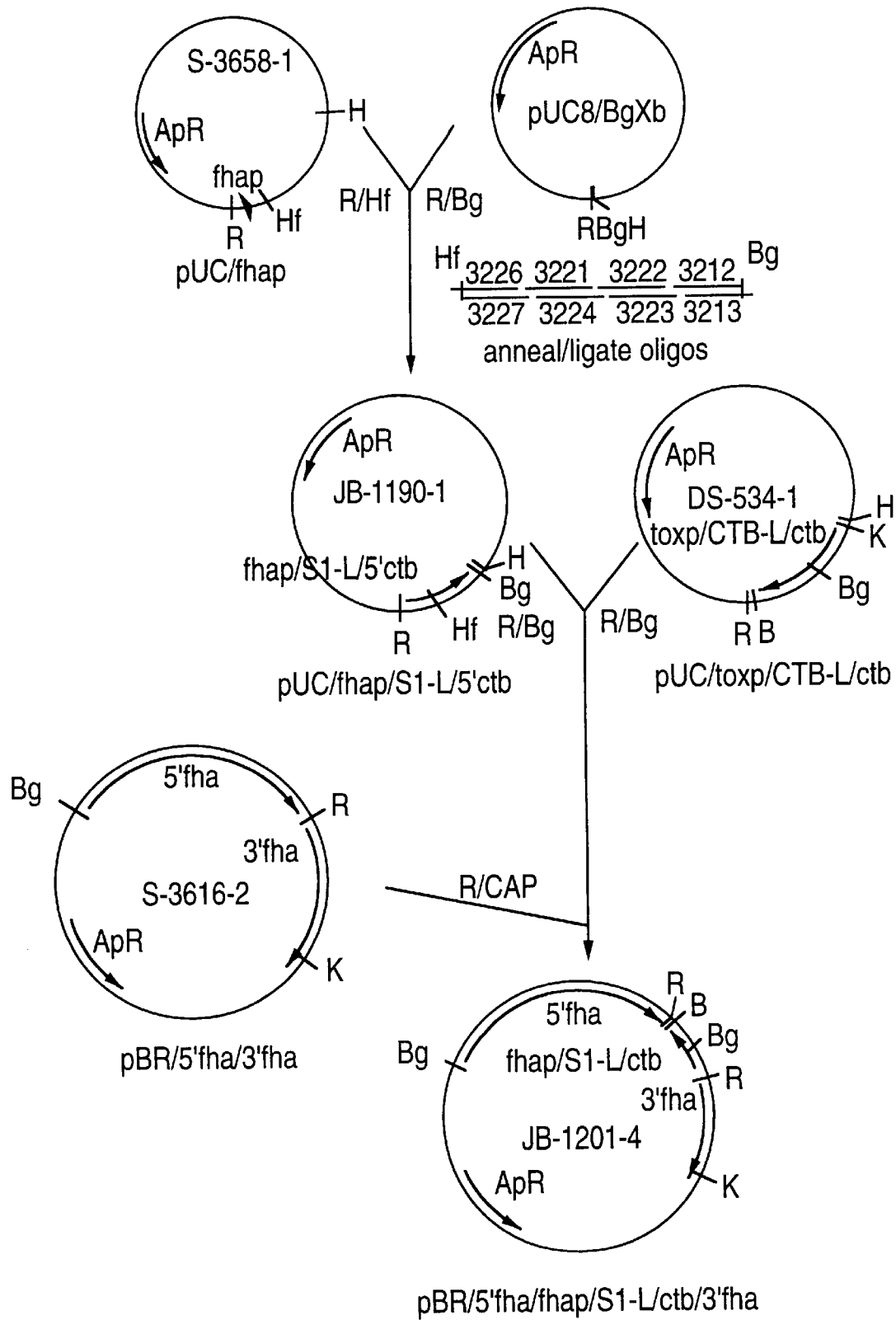
FIG. 10 shows the construction scheme for plasmid JB-1201-4 which contains the fhap/S1-L/ctb gene.

Plasmid S-3658-1 contains a ~210 bp EcoR I/Hinf I fragment of the fha promoter (FIG. 10). Oligonucleotides 3226.SL (SEQ ID NO: 41), 3221.SL (SEQ ID NO: 42), 3222.SL (SEQ ID NO: 43), 3212.SL (SEQ ID NO: 44), 3213.SL (SEQ ID NO: 45), 3223.SL (SEQ ID NO: 46), 3224.SL (SEQ ID NO: 47) and 3227.SL (SEQ ID NO: 48) (FIG. 11) contain part of the fha promoter, encode the pertussis toxin subunit Si leader peptide, and contain the first ~70 bp of the ctb gene encoding the mature cholera toxin B subunit protein. Plasmid pUC8/BgXb is a pUC8 derived plasmid with extra restriction enzyme sites for Bgl II and Xba I in the multiple cloning site (FIG. 10). The oligonucleotides were kinased, annealed, and ligated with the EcoR I/Hinf I fha promoter fragment into pUC8/BgXb which had been digested with EcoR I and Bgl II. Plasmid JB-1190-1 thus contains the fhap/S1-L/5'ctb hybrid gene on a ~414 bp EcoR I/Bgl II fragment. Plasmid DS-534-1 was digested with Bgl II and EcoR I to excise the ~250 bp 3'-ctb fragment, which was ligated with the EcoR I/Bgl II hybrid gene fragment into S-3616-2, which had been digested with EcoR I and dephosphorylated. The resulting plasmid JB-1201-4 thus contains the complete fha/S1-L/ctb hybrid gene between the fha flanking regions, in a reverse orientation with respect to the flanking regions (FIG. 10). This plasmid was used to introduce the fhap/S1-L/ctb hybrid gene into the fha locus of B. pertussis, generating strain 694-54.

Example 7

This Example illustrates the construction of plasmid JB-1141-5 which contains the fha/PRN-L/ctb hybrid gene.

Figure 12:
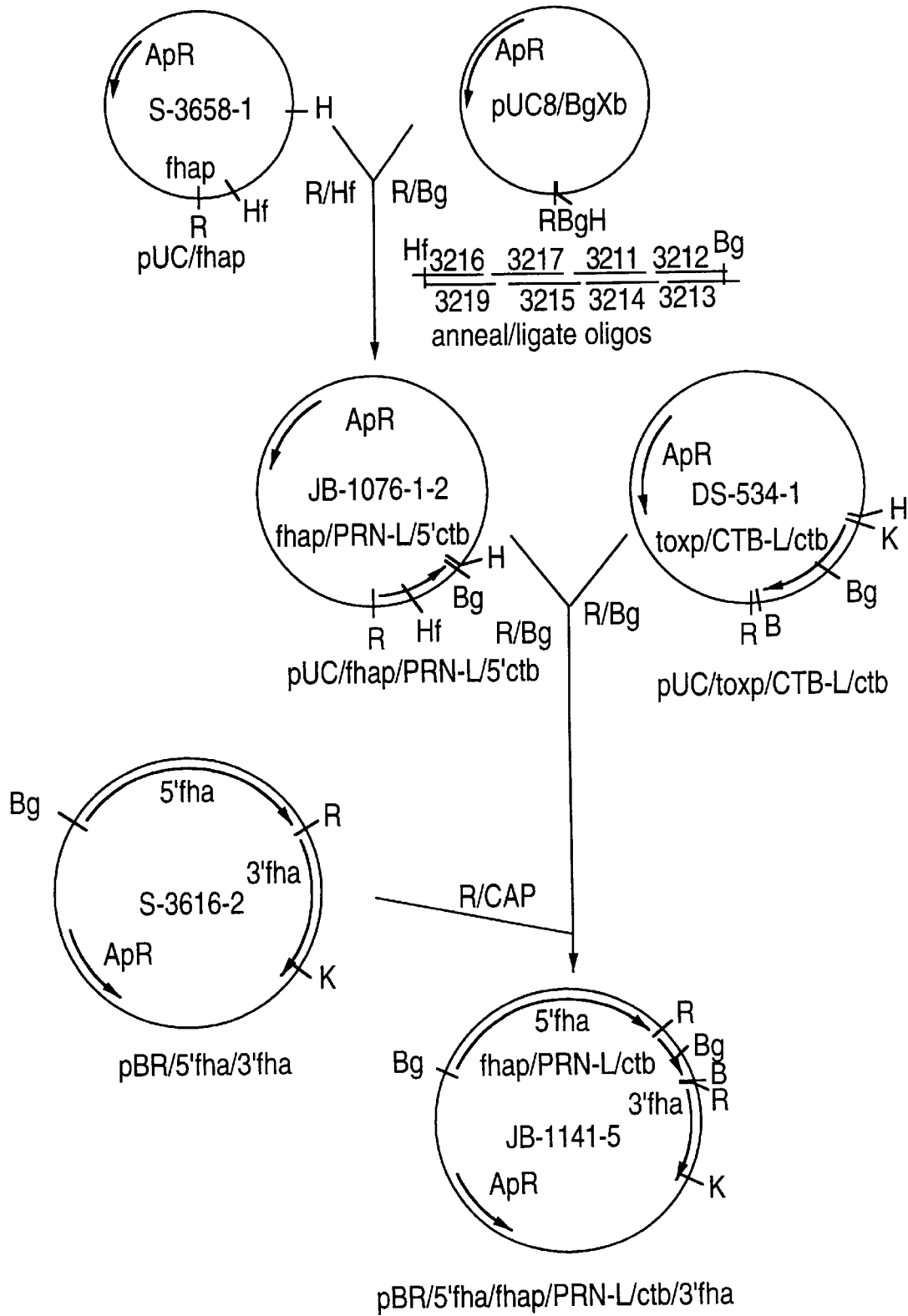
FIG. 12 shows the construction scheme for plasmid JB-1141-5 which contains the fha/PRN-L/ctb gene.

Oligonucleotides 3216.SL (SEQ ID NO: 49), 3217.SL (SEQ ID NO: 50), 3211.SL (SEQ ID NO: 51), 3212.SL (SEQ ID NO: 52), 3213.SL (SEQ ID NO: 53), 3214.SL (SEQ ID NO: 54), 3215.SL (SEQ ID NO: 55) and 3219.SL (SEQ ID NO: 56) contain part of the fha promoter, encode the pertactin leader peptide, and contain the first ~70 bp of the ctb gene encoding the mature cholera toxin B subunit protein (FIG. 13). The oligonucleotides were kinased, annealed, and ligated with the 210 bp EcoR/Hinf I fha promoter fragment from S-3658-1 (FIG. 12), into pUC8/BgXb which had been digested with EcoR I and Bgl II. Plasmid JB-1076-1-2 contains the fha/PRN-L/5'ctb hybrid gene on a ~414 bp EcoR I/Bgl II fragment and was ligated with the remainder of the ctb gene, excised from DS-534-1 on a ~250 bp Bgl II/EcoR I fragment, into the S-3616-2 vector which had been digested with EcoR I and dephosphorylated. The resulting plasmid JB-1141-5 (FIG. 12) thus contains the complete fha/PRN-FL/ctb gene between the fha flanking regions and was used to insert the hybrid gene into the fha locus of B. pertussis, generating strain 694-46.

Example 8

This Example illustrates the generation of recombinant B. pertussis strains.

B. pertussis strain 29-8 (ATCC 53,973) is a tox-deleted derivative of strain 10536 and is described in ref. 20. This strain was used as the host strain for genomic introduction of plasmids DS-546-1 (toxp/CTB-L/ctb), DS-729-1-1 (toxp/S1-L/ctb) and DS-729-2-1 (toxp/PRN-L/ctb). B. pertussis strain 590-508 is an fha-and tox-deleted derivative of strain 10536 and was used to genomically introduce plasmids JB-898-2-1 (fhap/CTB-L/ctb), JB-1201-4 (fhap/S1-L/ctb), and JB-1141-5 (fhap/PRN-L/ctb). Plasmids were introduced into the B. pertussis strains by electroporation as described by Zealey et al. (ref. 5 and 20). A single cross-over event resulted in integration of the entire plasmid generating $str^S Ap^R ctb^+$ strains. Selecting on streptomycin (100 $\mu$g ml$^{-1}$) resulted in a second homologous recombination event which deletes all plasmid sequences and generated strains 694-4, 694-12, 694-46, and 694-54 respectively. Strain 694-46 has been deposited with ATCC (ATCC 55,654). The second cross-over did not occur for strains 492-320 and 492-363, thus these strains include the entire plasmids DS-546-1 and JB-898-2-1 respectively.

The identification of the recombinant B. pertussis strains obtained and their derivations are summarized in Table 1 below.

Example 9

This Example illustrates a Southern blot analysis of recombinant B. pertussis strains to confirm the correct chromosomal location of the integrated genes.

Chromosomal DNA was isolated from B. pertussis strains 10536, 694-4, 694-12, 694-46, and 694-54, digested with restriction enzyme Bgl II,, electrophoresed, and transferred to Gene Screen Plus (Dupont). The blot was hybridized with a ~300 bp Bgl II/BamH I ctb-specific probe and the results are shown in FIG. 14. The appearance of a ctb-specific 1.5 kb Bgl II fragment confirmed the correct location of integration of the toxp/S1-L/ctb and toxp/PRN-L/ctb genes at the tox locus of B. pertussis strains 694-4 and 694-12 respectively. The appearance of a specific 11 kb Bgl II fragment confirmed the correct location of the fhap/S1-L/ctb and fha/PRN-L/ctb hybrid genes at the fha locus in B. pertussis strains 694-54 and 694-46 respectively.

Example 10

This Example illustrates the growth of recombinant B. pertussis strains and expression of cholera toxin B subunit.

Recombinant B. pertussis strains were grown in modified Stainer-Scholte medium containing 0.2% heptakis (2,4-O-dimethyl) β-cyclodextrin (ref. 21) in 10 ml culture. 1 ml of culture was centrifuged at 12,000×g for 4 min and the resulting supernatant was analysed by ELISA, SDS PAGE, and/or Western blot. The cell pellets were resuspended in 1 ml of media and lysed by sonication at 25$\mu$ for 45 sec, on ice with a Soniprep model 150 sonicator. Then, the cell debris was removed by centrifugation at 12000×g for 4 min, and the supernatant removed and analysed by ELISA.

The level of expression of cholera toxin B subunit from various B. pertussis strains is shown in Table 2 below.

Example 11

This Example illustrates the ELISA assay used for the quantitation of cholera toxin B expression.

Nunc Maxisorp 96 well plates were coated with monosialoganglioside—GM1 (Sigma) and incubated overnight at room temperature. The plates were washed and blocked with PBS containing 0.1% BSA for 45 min at room temperature. Two-fold serial dilutions of samples were added and the plates incubated for 1 h at room temperature.

Cholera toxin B (List Biologicals #103C), growth media, wild-type B. pertussis supernatant and cell pellets were used as standard and controls. CTB was detected using goat anti-choleragenoid (anti-CTB, List Biologicals #GAC-01C) as primary antibody and HRP-conjugated affinity purified rabbit anti-goat IgG as secondary antibody.

Example 12

This Example illustrates the analysis of the expressed recombinant proteins by SDS-PAGE and Western blot.

Culture supernatants were acetone-precipitated and resuspended in 0.1 volume of SDS lysis buffer. An equal volume of 2×Laemmli sample buffer was added and the samples were either resolved directly on a 17.5% SDS PAGE gel or boiled for 5 min, before being resolved to convert the CTB pentamer to the monomeric form. Cell pellets were resuspended in 0.1 volume of SDS lysis buffer, an equal volume of 2×Laemmli sample buffer added, and the samples treated as above.

For Western blot analysis, proteins were transferred onto Gene Screen Plus nylon membranes (Dupont) and probed with goat anti-choleragenoid IgG antibody (anti-CTB, List Biologicals #GAC-01C). Detection was performed with alkaline phosphatase-conjugated donkey anti-goat IgG, using dig chemiluminescence (Boehringer Mannheim). A cholera toxin standard (Sigma) contained both CTA and CTB.

FIG. 9 shows the expression of CTB as a pentamer in culture supernatants of strain 694-46 (fha/PRN-L/ctb). The identity of the cholera toxin is indicated by the correct molecular weight; specific-reactivity with anti-CTB antiserum and the conversion of the pentameric form of cholera toxin B subunit protein to the monomeric form by boiling.

SUMMARY OF THE DISCLOSURE

In summary of this disclosure, the present invention provides a novel gene product expression method having particular application to Bordetella species. Modifications are possible within the scope of this invention.

TABLE 1

Recombinant B. pertussis strains

| Strain | Genotype | Genetic Locus | Plasmid Used |
|---|---|---|---|
| 492-320 | toxp/CTB-L/ctb | tox | DS-546-1 |
| 492-363 | fhap/CTB-L/ctb | fha | JB-898-2-1 |
| 694-4 | toxp/S1-L/ctb | tox | DS-729-1-1 |
| 694-12 | toxp/PRN-L/ctb | tox | DS-729-2-1 |
| 694-54 | fhap/S1-L/ctb | fha | JB-1201-4 |
| 694-46 | fhap/PRN-L/ctb | fha | JB-1141-5 |

TABLE 2

Cholera toxin B expression from recombinant B. pertussis strains

| Plasmid | Strain | promoter | leader | CTB Production (ng/ml) secreted | internal |
|---|---|---|---|---|---|
| DS-546-1 | 492-320 | tox | CTB | 2.7 | 0 |
| DS-729-1-1 | 694-4 | tox | S1 | 1 ± 0.5 | 9.7 ± 12.9 |
| DS-729-2-1 | 694-12 | tox | PRN | 3.3 ± 7.3 | 44.9 ± 71.2 |
| JB-898-2-1 | 492-363 | fha | CTB | 5.4 | 9.0 |
| JB-1201-4 | 694-54 | fha | S1 | 116.4 ± 41.3 | 59.7 ± 14.1 |
| JB-1141-5 | 694-46 | fha | PRN | 11,287 ± 3,029.7 | 5,509.8 ± 785.4 |

REFERENCES

1. Johnson and Burns. 1994. J. Bacteriol. 176: 5350.
2. Locht et al. 1992. EMBO J. 11: 3175.
3. EP patent application 523 976.
4. EP patent application 453 216.
5. Zealey et al. 1992. Appl. Environ. Microbiol. 58: 208.
6. Burnette. 1994. Structure 2: 151.
7. Holmgren et al. 1993. Vaccine 11: 1179.
8. Wu and Russell. 1994. Vaccine 12: 215.
9. Dertzbough and Elson. 1993. Infect. Immun. 61: 384.
10. Cardenas and Clement. 1993. Vaccine 11: 126.
11. Airaksinen et al. 1991. Biotechnology Lett 13: 305.
12. Lebens et al. 1993. Bio/Technology 11: 1574.
13. Burnette et al. 1991. Infect. Immun. 59: 4266.
14. Klauser et al. 1990. EMBO J. 1991.
15. Nicosia et al. 1986. Proc. Natl. Acad. Sci. (U.S.A.) 83: 4631.
16. Loosmore et al. 1989. Nucleic Acid. Res. 17: 8365.
17. Relman et al. 1989. Proc. Natl. Acad. Sci. (U.S.A.) 86: 2637.
18. Charles et al. 1989. Proc. Natl. Acad. Sci. (U.S.A.) 86: 3554.
19. Dams et al. 1991. Biochen. Biophys. Acta. 1090: 139.
20. Zealey et al. 1990. Bio/Technology 8: 1025.
21. Imaizumi et al. 1983. Infect. Immun. 41: 1138.
22. Nicosia et al. 1987. Infect. Immun. 55: 963.
23. Makoff et al. 1990. Bio/Technology 8: 1030.
24. Domenighimi et al. 1990. Molec. Microbiol. 4: 787.
25. Watson, M. 1984. Nucl. Acids. Res. 12: 5145.

What we claim is:
1. A nucleic acid molecule having the nucleotide sequence shown in FIG. 1 (SEQ ID No: 1).

* * * * *